United States Patent
Sørensen (10) Patent No.: US 6,660,215 B2
(45) Date of Patent: Dec. 9, 2003

(54) PLANT FOR PRODUCING A WEB-SHAPED PRODUCT OF FIBERS AND POWDER

(75) Inventor: Birger Elmgaard Sørensen, Vejle (DK)

(73) Assignee: M&J Fibretech A/S, Horsens (DK)

(*) Notice: Subject to any disclaimer, the term of this patent is extended or adjusted under 35 U.S.C. 154(b) by 313 days.

(21) Appl. No.: 09/827,281

(22) Filed: Apr. 6, 2001

(65) Prior Publication Data

US 2001/0042948 A1 Nov. 22, 2001

Related U.S. Application Data

(63) Continuation of application No. PCT/DK99/00527, filed on Oct. 6, 1999.

(30) Foreign Application Priority Data

Oct. 6, 1998 (DK) .......................... 1998 01264

(51) Int. Cl.⁷ .............................. A61F 13/15; B27N 3/00
(52) U.S. Cl. ...................... 264/518; 264/121; 425/83.1
(58) Field of Search ................... 264/518, 121; 425/80.1, 81.1, 82.1, 83.1

(56) References Cited

U.S. PATENT DOCUMENTS

| | | | |
|---|---|---|---|
| 4,640,810 A | 2/1987 | Laursen et al. | 264/518 |
| 5,017,324 A | 5/1991 | Kaiser et al. | 264/510 |
| 5,102,585 A * | 4/1992 | Pieper et al. | 264/37.29 |
| 5,227,107 A * | 7/1993 | Dickenson et al. | 264/113 |
| 5,429,788 A * | 7/1995 | Ribble et al. | 264/510 |
| 5,432,000 A | 7/1995 | Young, Sr. et al. | 428/372 |
| 5,445,777 A * | 8/1995 | Noel et al. | 264/113 |
| 5,471,712 A | 12/1995 | Kroyer | 19/304 |
| 5,514,324 A | 5/1996 | Bachar | 264/518 |
| 6,207,099 B1 * | 3/2001 | Rooyakkers et al. | 264/518 |
| 6,267,575 B1 * | 7/2001 | Rooyakkers et al. | 425/83.1 |

FOREIGN PATENT DOCUMENTS

| | | |
|---|---|---|
| EP | 0 202 472 B1 | 8/1989 |
| EP | 0 439 012 A2 | 7/1991 |
| EP | 0 678 608 A1 | 10/1995 |
| WO | WO 96/07792 | 3/1996 |
| WO | WO 96/10663 | 4/1996 |

* cited by examiner

Primary Examiner—Mary Lynn Theisen
(74) Attorney, Agent, or Firm—Pennie & Edmonds LLP (57) ABSTRACT

This invention relates to a plant used to form an air-laid web of fibers and a powder on a running endless forming wire that is air-permeable and operates mainly horizontally, wherein the plant includes a suction unit positioned under the forming wire; a forming head with a perforated base positioned above the forming wire; at least one fiber feed duct using air flow from the fiber source to feed the fiber into the forming head; and at least one powder feed duct to feed powder by means of air flow from the powder source into the forming head.

22 Claims, 7 Drawing Sheets

PLANT FOR PRODUCING A WEB-SHAPED PRODUCT OF FIBERS AND POWDER

CROSS-REFERENCE TO RELATED APPLICATION

This application is a continuation of International Application No. PCT/DK99/00527, filed Oct. 6, 1999, the disclosure of which is hereby incorporated herein by express reference thereto.

FIELD OF THE INVENTION

This invention relates to a plant used to form an air-laid web of fibers and a powder on a running endless forming wire which is air-permeable and which operates mainly horizontally. The invention also comprises a suction unit positioned under the forming wire and a forming head positioned above the forming wire with a perforated base; at least one fiber feed duct to feed fiber by means of air flow from the fiber source into the forming head; and at least one powder feed duct to feed powder by means of air flow from the powder source into the forming head.

BACKGROUND OF THE INVENTION

A powder, such as a superabsorbent powder (SAP), is very widely used in products which are designed to absorb liquid. Such products include, for example, sanitary napkins, diapers, and incontinence products, which are all most effectively produced using an air-laid process. During the past few years, it has become common to add SAP directly during the air-laid process. The addition of SAP during the air-laid process is particularly suitable because the forming process takes place with the aid of air only, i.e., without the use of liquid that could inadvertently activate the SAP.

SAP has a higher density than fiber (usually 0.9 g/cm$^3$ to 1.3 g/cm$^3$) and the same consistency as sugar (particle size 100 microns to 800 microns). Therefore, when SAP is distributed in a forming head with fiber, SAP remains in the forming head for a significantly shorter time than the fiber. Furthermore, since SAP is a powder, conventional aspiration of SAP into the forming head on a jet of air allows irregular and random distribution of the powder in the forming head.

The accumulated effect of the above-mentioned characteristics is an uneven and inhomogeneous distribution of SAP in the finished product.

The applicant's EP Patent Application No. 94103336.7-2314 describes a forming head with rows of wings that, when running, sweep the fibers across the perforated base of the forming head. The rows of wings are positioned slightly at an angle relative to the direction of the machine to ensure that the fibers are evenly and uniformly distributed in the material to be laid on the form wire. It has been found that, even with the improved forming head, it is impossible to achieve a satisfactorily even and homogeneous distribution of SAP in the finished product. Cross-sectional distribution of fiber and SAP will normally be: plus or minus 3 percent fiber, plus or minus 7 percent SAP. If SAP is to have the optimum effect, however, it must be distributed precisely and homogeneously in the product. The product cannot optimally assimilate the SAP if the powder is not homogenously and precisely distributed, which leads to a reduction in the capacity to absorb liquid.

PCT Publication No. WO 96/07792 disclosed a method and system for producing air-laid paper webs with a specific content of powder, such as SAP. The system includes a perforated forming wire and two forming heads mounted above the forming wire. Each forming head is a bottomless box that receives a flow of air-fluidized fiber material through supply channels. The fiber material is distributed over the width of the wire inside the forming heads. A powder dispenser is used for sprinkling the powder over the entire width of the web delivered from the forming head. In one embodiment, two perforated drums are arranged in the forming head. When operating, the fiber flow is supplied to the drums that are simultaneously rotated so that the fibers are discharged through the perforated walls of the drums. Because the powder is sprinkled directly onto the forming wire, or in one embodiment, the drums, the heavier powder tends to fall down to the web faster than the lighter fibers, and therefore, it is not possible to obtain a satisfactory evenly distributed and homogeneous mixing of the powder and fibers.

PCT Publication No. WO 96/10663 discloses a plant and a process for dry-producing a web-formed product. The plant has three forming heads arranged on top of each other. Each of the forming heads has a perforated bottom that creates the ceiling of the underlying forming head, while the perforated bottom of the lower forming head is placed directly over a forming wire. In operation, the powder is introduced in an airflow led into the upper forming head and passed to the intermediate forming head through the perforated bottom of the upper forming head. Cellulose fibers are introduced into the intermediate forming head through a second airflow, The powder and cellulose fibers are then passed through the perforated bottom of intermediate forming head. Thermo-binding fibers in a third airflow are directed to the lower forming head, so that the powder, cellulose fibers, and thermo-binding fibers are passed through the perforated bottom of the lower forming head onto the forming wire. Using this process, the powder will not be mixed with fibers supplied to a forming head in one airflow and will not, therefore, result in a web with a satisfactory evenly distributed and homogeneous structure. In addition, the powder is blown into the upper forming head in a conventional way that initially produces an uneven distribution of the powder. It is not possible to produce a web having a high concentration of powder using this method as the powder will pass through the three perforated bottoms before contacting the the forming wire.

SUMMARY OF THE INVENTION

The present invention is directed to a plant for forming an air-laid web of fibers and powder including: an endless forming wire, wherein the wire is air-permeable and operates mainly horizontally; a suction unit positioned under the forming wire; a forming head positioned above the forming wire having a top and a perforated base, wherein at least one bushing is provided in the top; at least one fiber feed duct, wherein a first air flow carries a fiber source into a fiber inlet duct in the forming head; at least one powder feed duct, wherein a second air flow carries a powder source into the forming head; and at least one powder distributor located in the at least one power feed duct, configured and dimensioned to divide the second air flow into a plurality of finer jets of air, wherein the plurality of finer jets of air are aspirated into the forming head.

In one embodiment, the powder distributor is configured and dimensioned with a housing having a plurality of powder exits and at least one powder inlet duct for receiving the plurality of finer jets of air, wherein the at least one powder inlet duct is received into the at least one bushing of the forming head and connected to the powder feed duct. Preferably, the housing is configured and dimensioned in the form of a pipe having top and bottom ends and an inner cavity, wherein the bottom end has a hood, a skirt that fits tightly around the pipe, a funnel formed therein, and a base that closes off the bottom end, wherein the plurality of powder exits extend out therefrom. The housing can be mounted outside the forming head, and wherein each powder exit is connected to the powder distributor via a corresponding powder inlet duct. In one embodiment, at least one of the plurality of powder exits includes an adjustable valve, and in another embodiment, each powder exit includes an adjustable valve. The adjustable valve can be activated electromagnetically, hydraulically, or pneumatically.

The plurality of powder inlet ducts include top and bottom ends, and, in one embodiment, a portion of the plurality of powder inlet ducts have bottom ends extending past the fiber inlet duct. In another embodiment, the plurality of powder exits are positioned within the forming head.

The housing can be mounted vertically with respect to the plant, the base of the housing is facing downwards, and at least one of the plurality of powder exits is mounted inside the forming head. In this embodiment, the plurality of powder inlet ducts are configured and dimensioned to send the plurality of finer jets of air vertically into the forming head. In another embodiment, the plurality of powder inlet ducts are configured and dimensioned to send the plurality of finer jets of air horizontally into the forming head.

The first air flow has a direction that can be changed during operation. In one embodiment, the plurality of finer jets of air can be divided by an angled baffle plate. In another embodiment, the powder distributor includes a powder dosing apparatus.

Preferably, the powder source includes a superabsorbent powder.

The present invention is also directed to a device for producing a web of fibers and powder, including: a fiber feed duct for transporting a fiber feed; a powder feed duct; a powder distributor located in the powder feed duct to divide an air flow into a plurality of air flows; a forming head, having a perforated base, associated with the fiber feed duct and powder feed duct, capable of receiving and homogeneously mixing the plurality of air flows and fiber feed; and a continuous and air-permeable wire, upon which the homogenous mixture falls through the perforated base. In a preferred embodiment, the forming head further includes at least two rotating drums having perforated walls to receive and distribute the fiber feed, and a powder dosing apparatus is positioned near, or in another embodiment, inside, the at least two rotating drums.

Another aspect of the invention is directed to a method for forming a web of fibers and powder including: providing at least one fiber feed in a first air flow and at least one powder feed in a second air flow; dividing the second air flow into a plurality of finer jets of air, wherein the jets of air are guided into a forming zone; mixing the jets of air and the at least one fiber feed in the forming zone to form a homogeneous mixture, and directing the mixture downward onto a continuous and air-permeable wire.

BRIEF DESCRIPTION OF THE DRAWINGS

Further features and advantages of the invention can be ascertained from the following detailed description which is provided in connection with the attached drawings, wherein.

DETAILED DESCRIPTION OF THE INVENTION

In the following we assume that the plant is used to form a web of fiber and superabsorbent powder, SAP, and that the forming head is of the kind which, when running, distributes the fibers and the SAP along the perforated base of the forming head by means of rotating wings.

Figure 1:
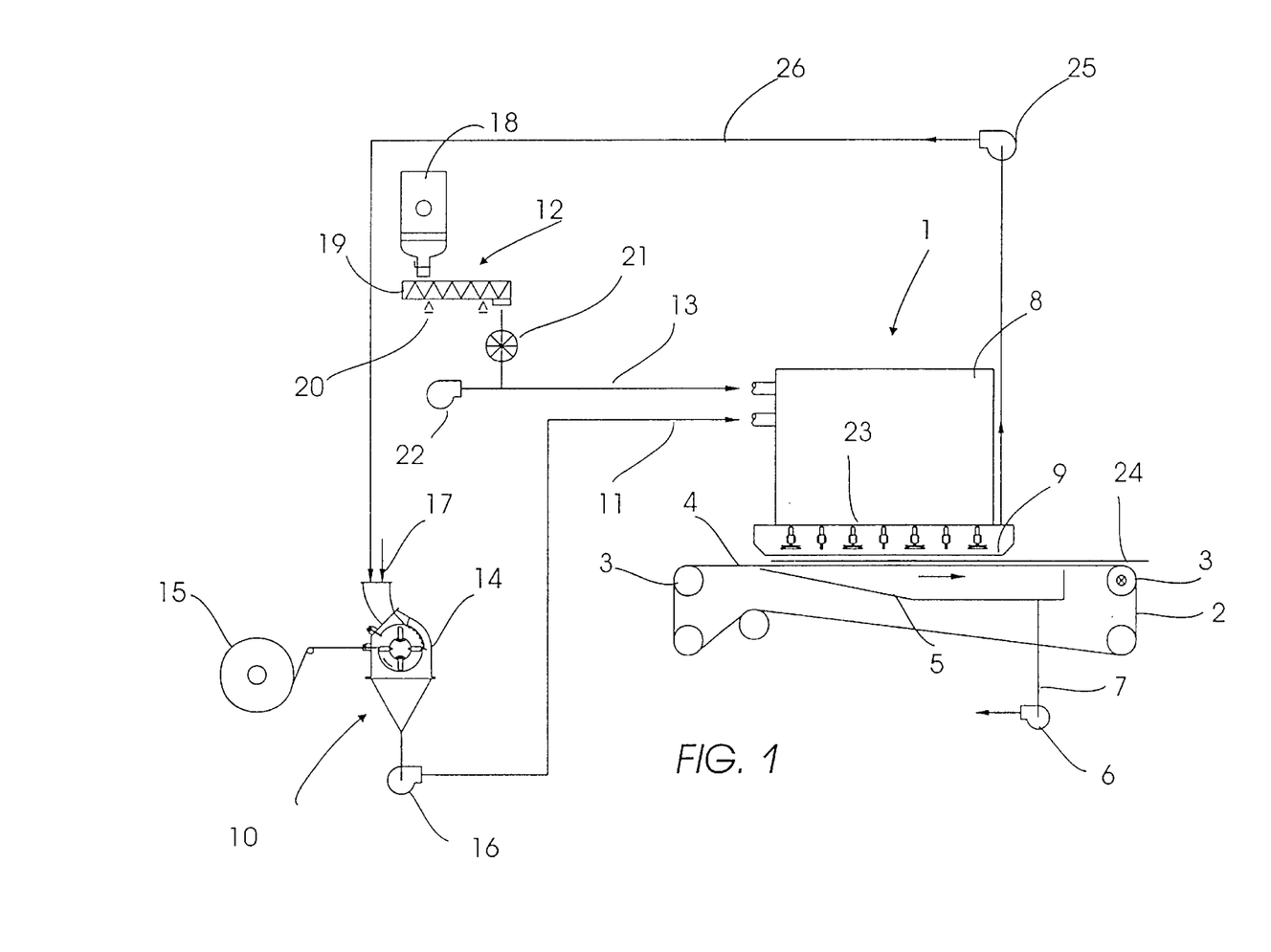
FIG. 1 is a schematic illustration of a conventional, commercially available plant with a forming head that forms an air-laid web of fiber and powder.

FIG. 1 shows a commercially available plant 1 without the benefits of the present invention including: an endless air permeable forming wire 2 that, when operating, runs over the rollers 3; a suction box 5, mounted under the upper part 4 of the forming wire, having an adjoined vacuum pump 6 that, with suction pipe 7, generates negative pressure in the suction box; a forming head 8, mounted above the forming wire 2, having a perforated base 9; a fiber source 10 that is connected to the forming head by a fiber feed duct 11; and a SAP source 12 that is connected to the forming head by a powder feed duct 13.

In this scenario, the fiber source 10 includes an ordinary defibrator 14 that receives raw material from a fiber stockpile 15. A ventilator 16 sends the defibrated fibers on a jet of air to the forming head 8 via the fiber feed channel 11. During this process, air is sucked out of the defibrator and substituted by replacement air via the air pipe 17.

The SAP source 12 includes a silo 18 for storing SAP. When the plant is in operating mode, the SAP is transported from the silo 18 on a conveyor 19 that continually weighs the desired amount of SAP with weighing cells 20. The SAP is transported via a rotating sluice 21 to a powder feed duct 13 and is blown by the ventilator 22 through the powder feed ducts into the forming head 8.

The fiber and SAP are aspirated simultaneously into the forming head when the plant is running and are transported from the suction box 5 down towards the base 9 of the forming head using both gravity and suction. As shown, the fiber and SAP then pass through seven rows of rotating wings 23 that send jets of falling material across the perforated base 9 of the forming head. The material is simultaneously distributed evenly over the perforated base 9 and gradually sucked down through the openings in base 9 by differential pressure in the forming head 8 and the suction box 5. New material is fed at the same rate into the forming head via the fiber feed duct 11 and the powder feed duct 13.

Most of the material then forms a web 24 on the upper part 4 of the forming wire 2, typically in the form of a mesh that is finer than a mesh formed by fiber or SAP separately. The upper part 4 of the forming wire 2 runs in the direction indicated by the arrow in FIG. 1 and transports the web 24 to the next phase of the process (not shown).

The SAP is aspirated into the forming head, resulting in a very irregular distribution. Furthermore, because the density of SAP is significantly greater than the density of fiber, the SAP falls relatively faster down to the base 9. In addition, the difference in density means that the wings 23 do not distribute the fibers and SAP equally over the base 9 and that the SAP falls more easily than the fiber through the openings in the perforated base 9. Under these conditions, the SAP in the web 24 is uneven and inhomogeneous; the quality of the final product is, therefore, not optimum.

During production, nits, i.e., knots, in the defibrated material are formed as a result of imperfect defibration in the defibrator 14 during transport to the forming head 8, or during the processes that take place within the forming head 8.

The nits reduce the quality of the finished product and are, therefore, extracted from the forming head 8 by a ventilator 25, inserted into a nits return duct 26 that connects the back end (in relation to the machine direction) of the forming head 8 to the defibrator 14.

It is to be noted that distribution of fiber in this plant according to the invention is just as efficient in a plant without nits extraction.

Figure 2:
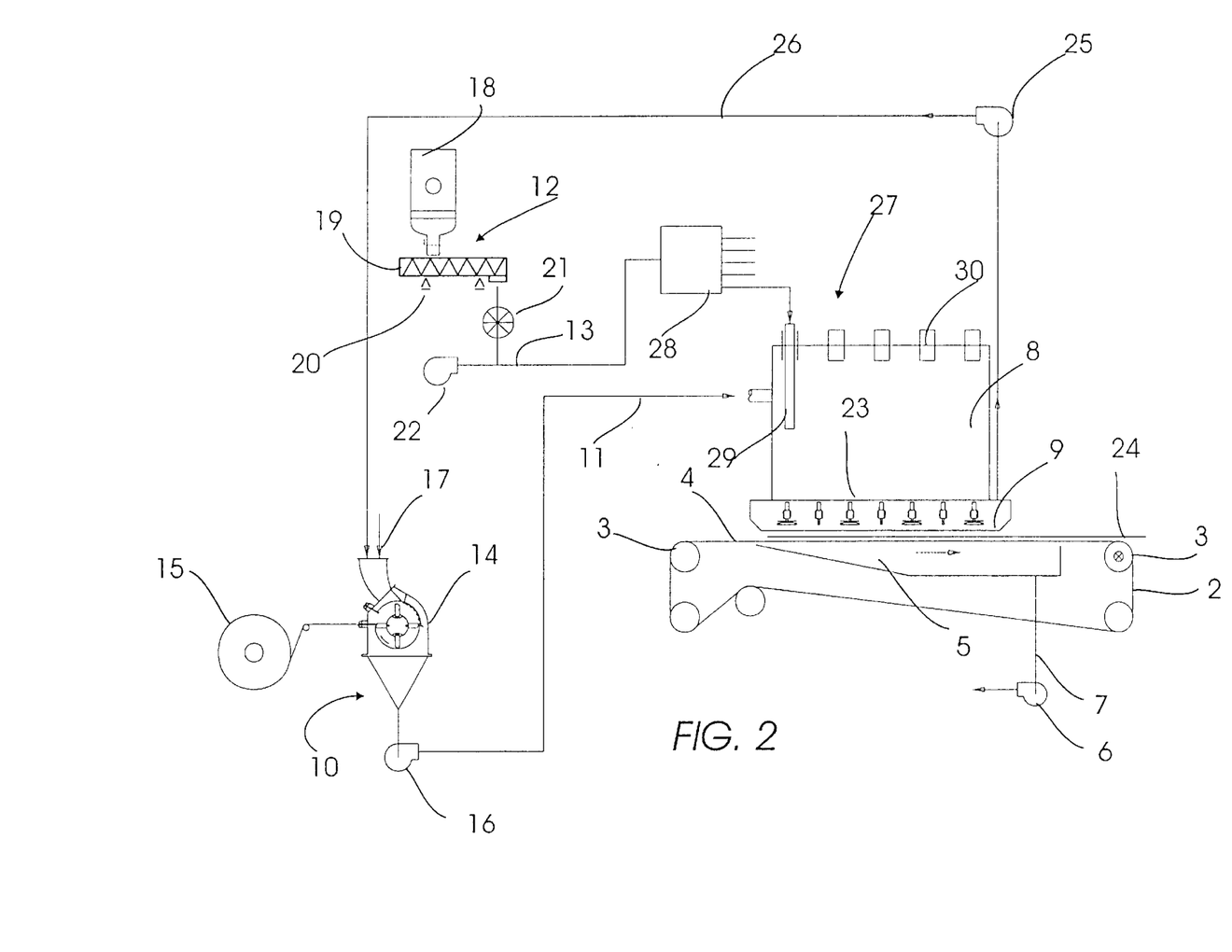
FIG. 2 is a schematic illustration of a plant with a forming head that forms an air-laid web of fiber and powder according to a first embodiment of the invention.
Figure 3:
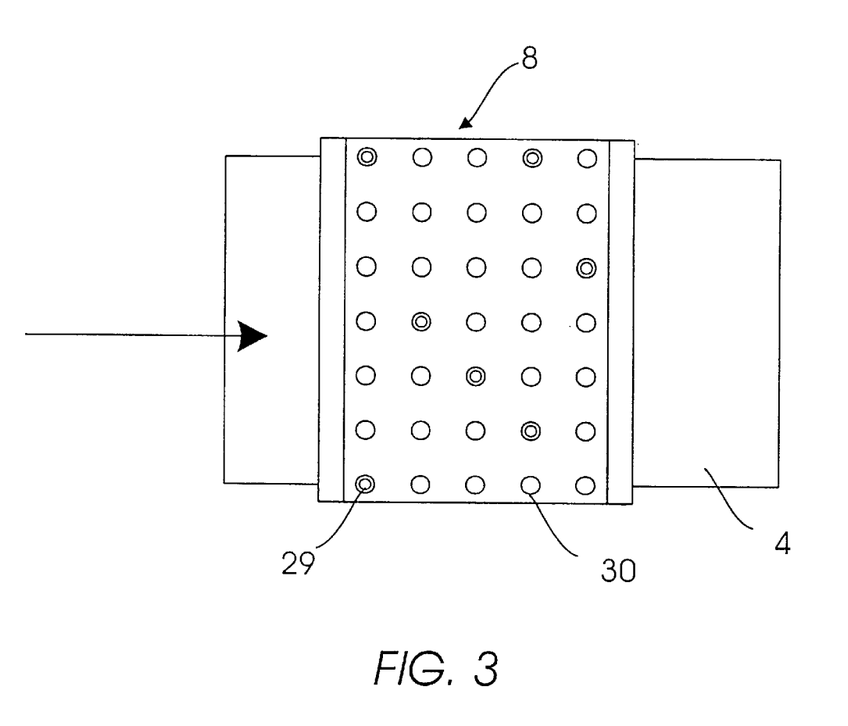
FIG. 3 shows an aerial view of FIG. 2.
Figure 4A:
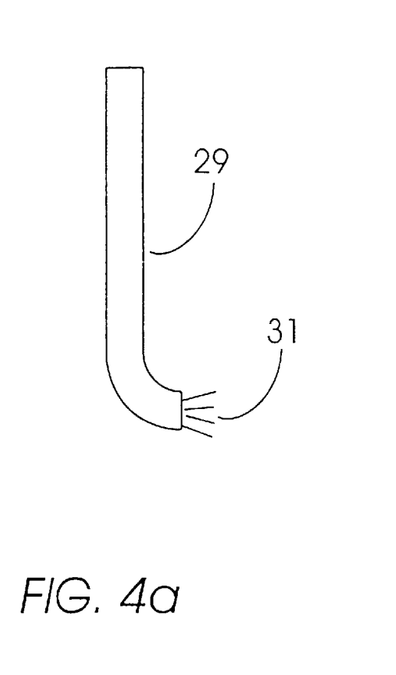
FIGS. 4a–d show a lateral view of four different constructions for inlet ducts for the plant in FIG. 2 according to the invention.
Figure 4B:
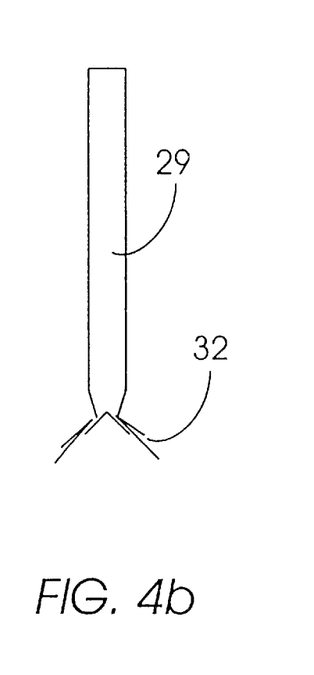
Figure 4C:
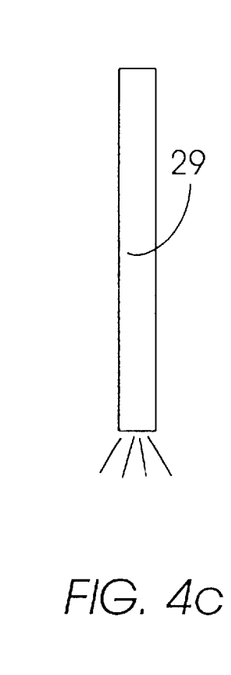
Figure 4D:
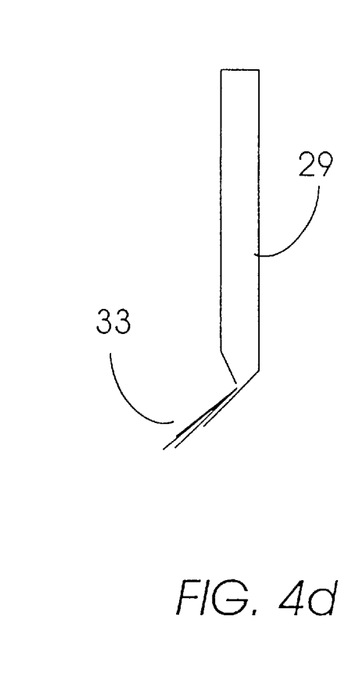

FIG. 2 shows the first embodiment of a plant 27 according to the invention. The plant has many of the same components as the commercially available plants discussed in FIG. 1 and, therefore, the like components have been given the same reference number.

Figure 5:
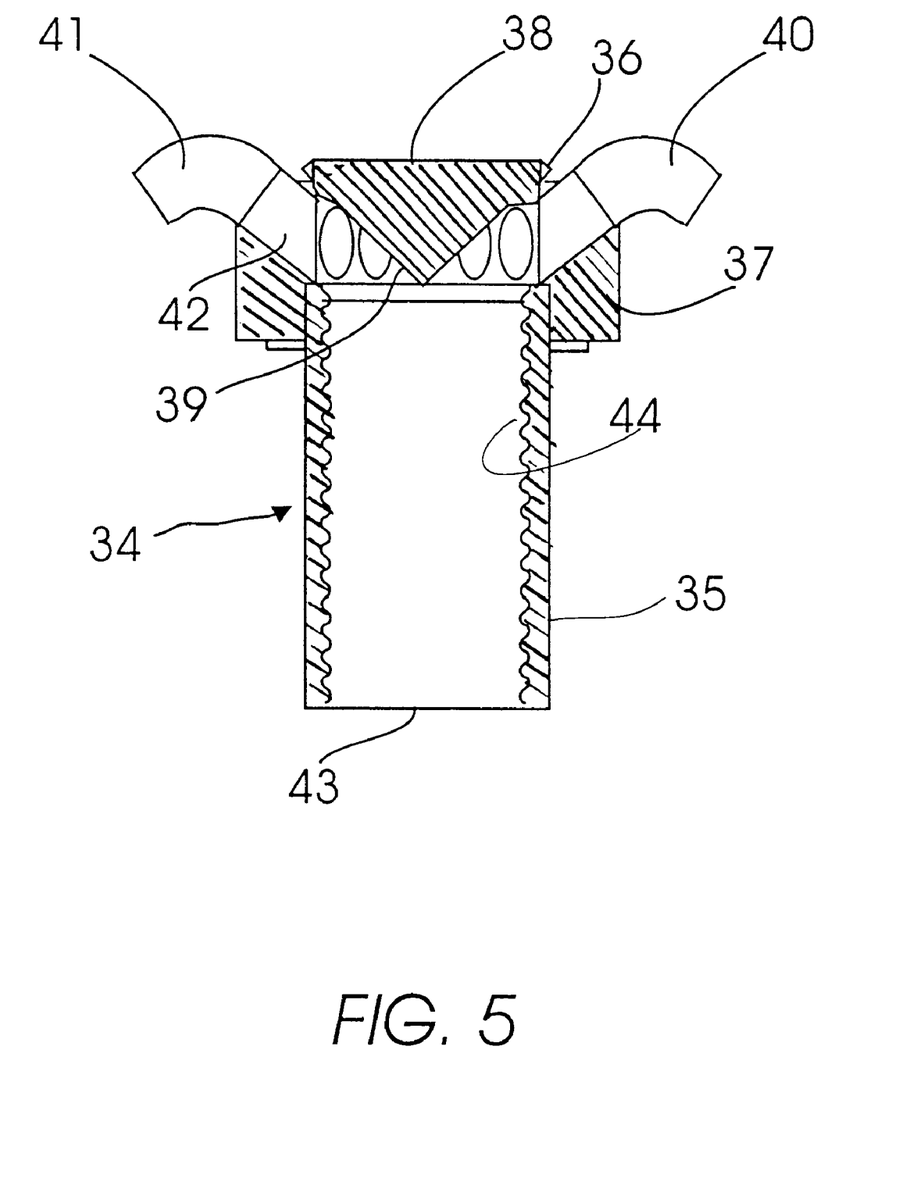
FIG. 5 shows a lateral cross-section of a powder distributor for the plant shown in FIG. 2.
Figure 6:
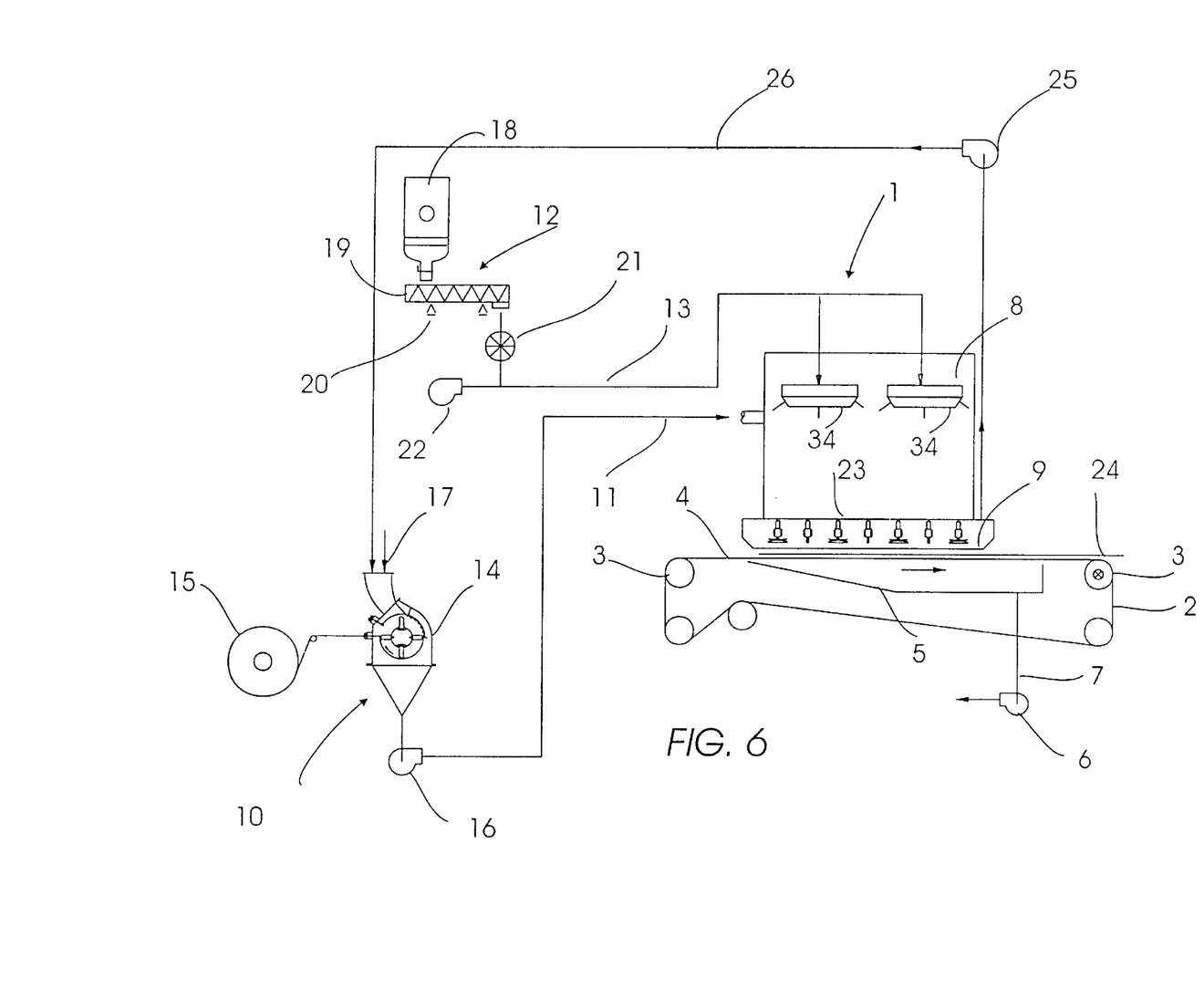
FIG. 6 is a schematic illustration of a plant with a forming head that forms an air-laid web of fiber and powder according to a second embodiment of the invention.

The powder distributor 28 is inserted in the powder feed duct 13. The main air jet in the powder distributor 28 divides the powder content into a number of finer jets of air, each of which is aspirated into the forming head through separate powder inlet ducts 29. FIG. 2 shows only one powder inlet duct, however, there will typically be several inlet ducts, each directed to a pre-designated strategic area of the forming head.

In this embodiment, the forming head 8, as shown in FIGS. 2 and 3, is provided with a plurality of bushings 30 that are designed for receiving a corresponding powder inlet duct 29. In FIG. 3, a powder inlet duct 29 is inserted down through the bushings 30 (marked with a double ring). The remaining bushings are closed off by a cover (not shown).

As shown in FIG. 2, the powder inlet duct 29 empties into the turbulent area where the air from the fiber feed duct 11 blows into the forming head 8. The fine jet of air containing SAP flows out of powder inlet duct 29 into relatively still air. This ensures that the fine jet of air can be directed precisely towards the strategically correct place within the forming head 8.

FIGS. 4*a*, 4*b*, 4*c*, and 4*d* illustrate examples of the different mouths of the powder inlet ducts 29 according to various embodiments of the invention.

FIG. 4*a* shows a powder inlet duct 29 with a lower curve 31 that sends the fine jet of air containing SAP either horizontally or diagonally into the forming head. This construction is advantageous when a powder inlet duct 29 is placed close to the inner wall of the forming head 8, as the air flow will rebound away from the wall, thus avoiding an uneven distribution of SAP in the forming head 8. At the same time, the direction of the incoming jet of air 11 can be adjusted during operation.

The jet of air can also be divided by an angled baffle plate 32, as shown in FIG. 4*b*. If the powder inlet duct 29 is placed directly above a row of the rotating wings 23, the SAP will blow directly into the material flowing over the perforated base 9 on both sides of the row of wings 23.

SAP can also be aspirated straight down between two rows of wings, as illustrated in FIG. 4*c*.

FIG. 4*d* depicts a mouth of the powder inlet duct 29 that is equipped with a diagonal baffle plate 33. The baffle plate 33 is designed to direct the fine jet of air towards an area of the perforated base 9 where a specific amount of SAP is to be added to the material flowing over the base 9. The direction of the jet of air can be adjusted while the machine is running, i.e., the jet can be directed towards other areas.

The powder inlet ducts can have a valve for regulating the volume of the jet of air through the respective inlet ducts. The valve will usually be a damper that can be activated either electromagnetically or with the aid of a hydraulic or pneumatic cylinder. The valves ensure that the pattern of powder-laden air in the forming head can be accurately regulated and constantly adjusted during operation.

As mentioned above, in commercially available plants SAP is aspirated uncontrolled and unevenly into the forming head. This means that the distribution of SAP in the product is more or less random and uneven and, thus, the quality of the product is diminished. Using a powder distribution plant in accordance with the invention, it is now possible to control the incoming jets and position the SAP exactly where required in the product, thus optimizing the product characteristics and raw material composition. The product achieves optimum high quality with an accurate and homogeneous SAP distribution, and, therefore, the product functions more uniformly optimizing the SAP consumption.

Any suitable technique known to those of ordinary skill in the art can be used for splitting the main jet of air in the fiber feed duct 11 into finer jets of air that are then aspirated under control via air powder inlet ducts 29 into the forming head 8, as described above.

FIG. 5 shows a lateral cross-section of preferred powder distributor 34 according to the invention. The powder distributor 34 has the formation of a pipe 35 with a hood 36, including a skirt 37 that fits tightly around the pipe 35 and a base 38 closing off the end of pipe 35. The inside of pipe 35 acts as a funnel 39. A plurality of powder exits 40 extend outwards from the periphery of the powder distributor 34. Each powder exit 40 comprises a nozzle 41 and a hole 42 that run diagonally into the casing of the hood near the air funnel 39 at the base 38.

The open end 43 of the pipe 35 is connected to the fiber feed duct 11 (not shown in FIG. 5) and each of the exit nozzles 40 is connected to the forming head via their own respective inlet ducts 29 (also not shown in FIG. 5).

During operation, the main jet of air from the fiber feed duct 11 flows into the powder distributor pipe 35. When it meets the base 38, the main air jet is divided into a plurality of identical finer jets of air, each of which flows out into a separate powder exit 40. From there, the fine jets of air flow into their own respective inlet ducts 29 and into the designated area of the forming head 8.

The inside surface of the pipe 35 is uneven 44. The uneven surface causes turbulence in the main air jet in the pipe 35, ensuring that the SAP is evenly and homogeneously suspended in the jet of air so that the finer jets of air in the powder exits 40 and powder inlet ducts 29 contain equal, specified quantities of SAP.

The pipe axis 35 of the powder distributor 34 is vertical. The force of gravity is neutral relative to the distribution of powder between the various powder exits 40. Furthermore, the base 38 of the powder distributor 35 may be positioned either outside or within the forming head and with the base 38 facing either the top or the bottom of the forming head 8.

FIG. 6 shows a preferred form of the invention shown in FIG. 2, and therefore, the same reference numbers have been employed for the identical components. FIG. 6 is a schematic illustration of two powder distributors 34, as shown in FIG. 5, positioned inside the forming head 8 with their bases 38 facing the bottom of the forming head 8. Placing the powder distributors 34 within the forming head 8 allows for an optimum utilization of space in the forming head 8 and the ensuing connection to the fiber feed duct 11 is simple and efficient. Another benefit of this preferred embodiment is that the powder is fed directly into the forming head 8 through the powder exits 40 which may be fitted with short powder inlet ducts 29.

Figure 7:
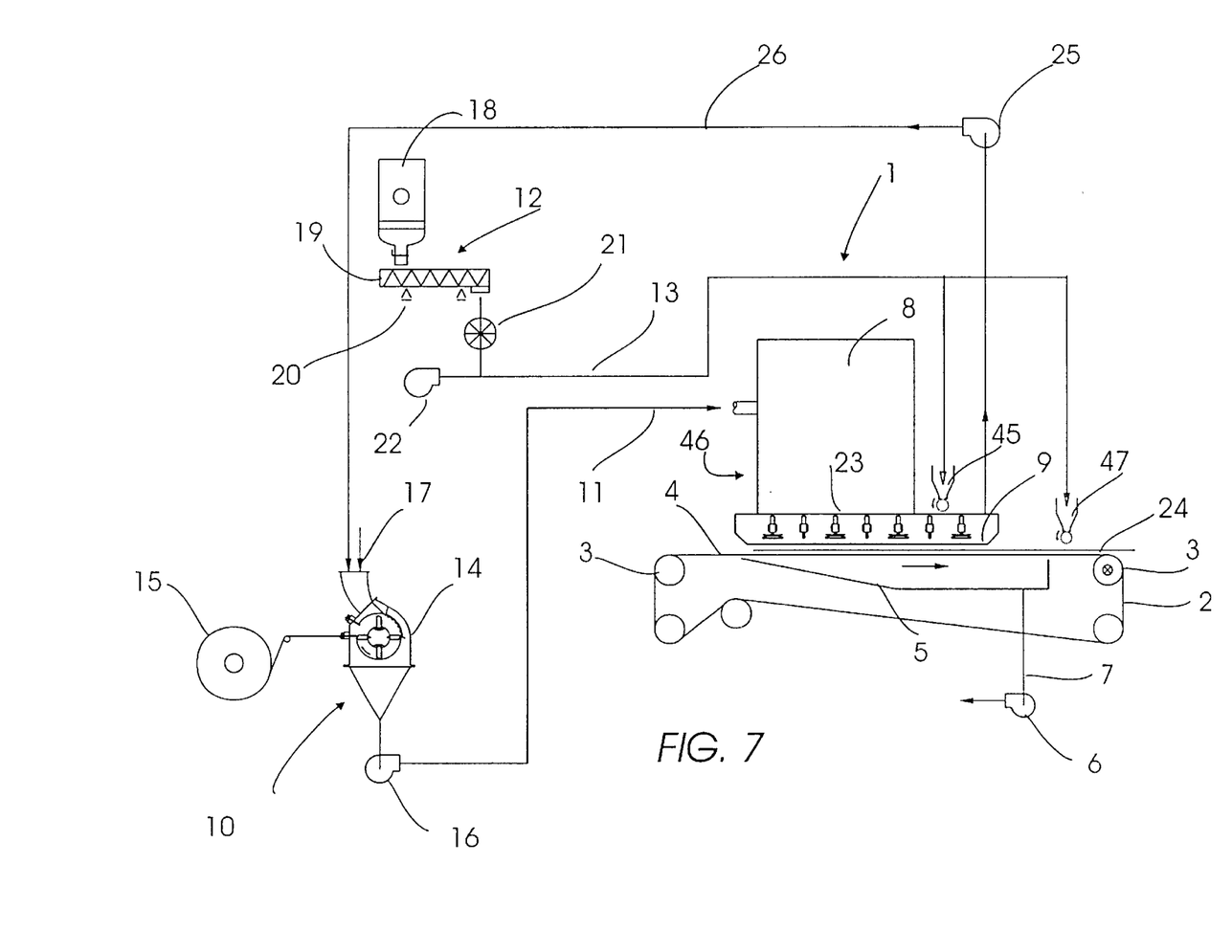
FIG. 7 is a schematic illustration of a plant with a forming head that forms an air-laid web of fiber and powder according to a third embodiment of the invention.

Another preferred form of the invention depicted in FIG. 2 is shown in FIG. 7 and uses the same reference numerals for like components. FIG. 7 shows a powder distributor 34 in the form of an established SAP dosing apparatus 45 which is fitted above an open section of the forming head housing 46, in close proximity to the space between two rows of rotating wings 23 that, in this case, lie at the back end (relative to the direction of the machine). A rotating feeding roller, which works like a sowing machine, distributes SAP along a line running at right angles to the machine direction. This concept advantageously ensures an very accurate distribution of SAP. In addition, the quantity of SAP transferred to the defibrator 14 that typically causes wear and tear can be reduced.

The SAP dosing apparatus 45 may be mounted either vertically or diagonally. In another embodiment, the SAP dosing apparatus can be mounted in a sealed section of the forming housing instead of in an open section.

The invention dictates that the SAP dosing apparatus 45 can be mounted anywhere in the forming head housing 8. In FIG. 7, the SAP dosing apparatus 45 is mounted in an open section of the forming head housing 46 that distributes fibers and SAP over the perforated base by means of rotating wings and the SAP dosing apparatus 45 can be mounted advantageously in an area close to the area where the fibers are distributed.

A second SAP dosing apparatus 47 can be mounted after the forming head 8 to dose a layer of SAP on top of the web already formed on the forming wire 2 in the area beyond the forming head housing 46. When a second SAP dosing apparatus 47 is mounted to produce a further web over the SAP layer, the resultant product will advantageously have an extra concentration of SAP in a central layer.

There are air-laid forming heads, not shown, in which the fiber is distributed through the perforated walls of rotating drums. In this case, mounting the SAP dosing apparatus 45 in an area very close to or within these drums is beneficial and ensures that the SAP is mixed with the fibers in the drums.

It is to be understood that the invention is not to be limited to the exact configuration as illustrated and described herein. For example, it should be apparent that a variety of forming heads would be suitable for use in the plant according to the invention. In addition, the invention is described assuming that the substance to be distributed in the product is SAP, however, the plant described in the invention could be used to distribute any other kind of powder or particulate material evenly and homogeneously in a web-formed fiber product. Accordingly, all expedient modifications readily attainable by one of ordinary skill in the art from the disclosure set forth herein, or by routine experimentation therefrom, are deemed to be within the spirit and scope of the invention as defined by the appended claims.

What is claimed is:

1. A plant for forming an air-laid web of fibers and powder comprising:

an endless forming wire, wherein the wire is air-permeable and operates mainly horizontally;

a suction unit positioned under the forming wire;

a forming head positioned above the forming wire having a top and a perforated base, wherein at least one bushing is provided in the top;

at least one fiber feed duct, wherein a first air flow carries a fiber source into a fiber inlet duct in the forming head;

at least one powder feed duct, wherein a second air flow carries a powder source into the forming head; and at least one powder distributor located in the at least one powder feed duct, configured and dimensioned to divide the second air flow into a plurality of finer jets of air, wherein the plurality of finer jets of air are introduced into the forming head.

2. The plant of claim 1, wherein the powder distributor is configured and dimensioned with a housing having a plurality of powder exits and at least one powder inlet duct for receiving the plurality of finer jets of air, wherein the at least one powder inlet duct is received into the at least one bushing of the forming head and connected to the powder feed duct.

3. The plant of claim 2, wherein the housing is configured and dimensioned in the form of a pipe having top and bottom ends and an inner cavity, wherein the bottom end has a hood, a skirt that fits tightly around the pipe, a funnel formed therein, and a base that closes off the bottom end, wherein the plurality of powder exits extend out therefrom.

4. The plant of claim 2, wherein at least one of the plurality of powder exits comprises an adjustable valve.

5. The plant of claim 4, wherein each powder exit comprises an adjustable valve.

6. The plant of claim 4, wherein the adjustable valve can be activated electromagnetically, hydraulically, or pneumatically.

7. The plant of claim 2, wherein the housing is mounted outside the forming head, and wherein each powder exit is connected to the powder distributor via a corresponding powder inlet duct.

8. The plant of claim 2, wherein the plurality of powder inlet ducts comprise top and bottom ends, and wherein a portion of the plurality of powder inlet ducts have bottom ends extending past the fiber inlet duct.

9. The plant of claim 2, wherein the plurality of powder exits are positioned within the forming head.

10. The plant of claim 2, wherein the housing is mounted vertically with respect to the plant, the base of the housing is facing downwards, and at least one of the plurality of powder exits is mounted inside the forming head.

11. The plant of claim 2, wherein the plurality of powder inlet ducts are configured and dimensioned to send the plurality of finer jets of air vertically into the forming head.

12. The plant of claim 2, wherein the plurality of powder inlet ducts are configured and dimensioned to send the plurality of finer jets of air horizontally into the forming head.

13. The plant of claim 1, wherein the first air flow has a direction that can be changed during operation.

14. The plant of claim 2, wherein the plurality of finer jets of air can be divided by an angled baffle plate.

15. The plant of claim 1, wherein the powder source comprises a superabsorbent powder.

16. The plant of claim 1, wherein the powder distributor comprises a powder dosing apparatus.

17. A device for producing a web of fibers and powder, comprising:

a fiber feed duct for transporting a fiber feed;

a powder feed duct;

a powder distributor located in the powder feed duct to divide an air flow into a plurality of air flows;

a forming head, having a perforated base, associated with the fiber feed duct and powder feed duct, capable of receiving and homogeneously mixing the plurality of air flows and fiber feed; and a continuous and air-permeable wire, upon which the homogenous mixture falls through the perforated base.

18. The device of claim 17, wherein the forming head further comprises at least two rotating drums having perforated walls to receive and distribute the fiber feed, and wherein a powder dosing apparatus is positioned near the at least two rotating drums.

19. The device of claim 17, wherein the forming head further comprises at least two rotating drums having perforated walls to receive and distribute the fiber feed, and wherein a powder dosing apparatus is positioned inside the rotating drums.

20. A method for forming a web of fibers and powder comprising:

providing at least one fiber feed in a first air flow and at least one powder feed in a second air flow;

dividing the second air flow into a plurality of finer jets of air, wherein the jets of air are guided into a forming zone;

mixing the jets of air and the at least one fiber feed in the forming zone to form a homogeneous mixture, and directing the mixture downward onto a continuous and air-permeable wire.

21. The plant of claim 1, wherein the plurality of finer jets of air are aspirated into the forming head.

22. The plant of claim 1, wherein the plurality of finer jets of air are fed directly into the forming head.

* * * * *